(12) United States Patent
Lutscher et al.

(10) Patent No.: US 12,377,540 B2
(45) Date of Patent: Aug. 5, 2025

(54) METHOD AND SYSTEM FOR PERFORMING A PREDETERMINED TASK USING A ROBOT

(71) Applicant: KUKA Deutschland GmbH, Augsburg (DE)

(72) Inventors: Ewald Lutscher, Augsburg (DE); Mario Daniele Fiore, Augsburg (DE)

(73) Assignee: KUKA Deutschland GmbH (DE)

( * ) Notice: Subject to any disclaimer, the term of this patent is extended or adjusted under 35 U.S.C. 154(b) by 621 days.

(21) Appl. No.: 17/431,593

(22) PCT Filed: Jan. 24, 2020

(86) PCT No.: PCT/EP2020/051708
§ 371 (c)(1),
(2) Date: Aug. 17, 2021

(87) PCT Pub. No.: WO2020/169302
PCT Pub. Date: Aug. 27, 2020

(65) Prior Publication Data
US 2022/0111520 A1    Apr. 14, 2022

(30) Foreign Application Priority Data

Feb. 22, 2019   (DE) ..................... 10 2019 202 456.4

(51) Int. Cl.
*B25J 9/16* (2006.01)
*A61B 34/32* (2016.01)
*B25J 15/00* (2006.01)

(52) U.S. Cl.
CPC ............ *B25J 9/1643* (2013.01); *A61B 34/32* (2016.02); *B25J 9/1607* (2013.01); *B25J 9/1633* (2013.01); *B25J 9/1651* (2013.01); *B25J 15/0019* (2013.01)

(58) Field of Classification Search
CPC ...... B25J 9/1643; B25J 9/1607; B25J 9/1633; B25J 9/1651; B25J 15/0019; B25J 13/085;
(Continued)

(56) References Cited

U.S. PATENT DOCUMENTS 8,774,969 B2    7/2014  Schreiber
2007/0120512 A1 5/2007  Albu-Schaffer et al.
(Continued)

FOREIGN PATENT DOCUMENTS

CN          108139747 A     6/2018
DE   10 2009 007 181 A1    8/2010
(Continued)

OTHER PUBLICATIONS

Arne Wahrburg et al, "Sensorless Null-Space Admittance Control for Redundant Manipulators", Robotics in the Era of Digitalisation : 47th International Symposium on Robotics : Jun. 21-22, 2016, Messe München, Entrance East, Munich, Germany, DE, (Jun. 21, 2016), ISBN 978-3-8007-4231-8, XP055688503 [X] 1-6,8,9 paragraph [0001]—paragraph [0004].
(Continued)

*Primary Examiner* — Sihar A Karwan
(74) *Attorney, Agent, or Firm* — Dorton & Willis, LLP

(57) ABSTRACT

A method for carrying out a predetermined task using a robot, which is redundant with regard to the task. When the task is carried out, an admittance motion that is dependent on a force exerted externally on the robot and on a predetermined virtual mass, stiffness and/or damping is carried out in the zero space.

12 Claims, 1 Drawing Sheet

(58) Field of Classification Search
CPC .... B25J 9/16; B25J 9/06; B25J 9/1679; A61B 34/32
See application file for complete search history.

(56) References Cited

U.S. PATENT DOCUMENTS

| | | | |
|---|---|---|---|
| 2014/0081461 A1 | 3/2014 | Williamson et al. | |
| 2014/0379126 A1 | 12/2014 | Ueberle | |
| 2015/0081098 A1 | 3/2015 | Kogan | |
| 2016/0129588 A1* | 5/2016 | Pfaff | B25J 9/06 901/4 |
| 2020/0101604 A1 | 4/2020 | Lutscher | |

FOREIGN PATENT DOCUMENTS

| | | |
|---|---|---|
| DE | 10 2013 010 290 A1 | 12/2014 |
| DE | 10 2011 083 347 B4 | 8/2015 |
| DE | 10 2014 222 809 B3 | 1/2016 |
| DE | 102014226936 B3 | 3/2016 |
| DE | 10 2015 210 218 A1 | 12/2016 |
| DE | 10 2017 004 711 A1 | 11/2018 |
| JP | 2013054629 A | 3/2013 |
| KR | 1020110114526 A | 10/2011 |
| KR | 1020150032639 A | 3/2015 |
| WO | 2016193217 A1 | 12/2016 |

OTHER PUBLICATIONS

Luigi Villani et al, "Null-Space Impedance Control For Physical Human-Robot Interaction", CISM Courses and Lectures—International Centre for Mechanical Sciences, (Jan. 1, 2013), vol. 544, pp. 193-200, doi:10.1007/978-3-7091-1379-0_24, ISSN 0254-1971, XP055688501 [A] 1-9.

European Patent Office; Search Report in related International Patent Application No. PCT/EP2020/051708 dated May 19, 2020; 6 pages.

European Patent Office; Written Opinion in related International Patent Application No. PCT/EP2020/051708 dated May 19, 2020; 7 pages.

German Patent Office; Search Report in related German Patent Application No. 10 2019 202 456.4 dated Oct. 22, 2019; 6 pages.

Chinese Patent Office; Office Action in related Chinese Patent Application No. 202080015794.2 dated Aug. 3, 2023; 11 pages.

Korean Patent Office; Notice of Grounds for Rejection in related Korean Patent Application No. 10-2021-7029895 dated Mar. 10, 2025; 6 pages.

European Patent Office; Examination Report in related European Patent Application No. 20 702 254.2 dated Jul. 1, 2024; 9 pages.

A. Wahrburg, J. Boes, B. Matthias, F. Dai and H. Ding, "Sensorless Null-Space Admittance Control for Redundant Manipulators," Proceedings of ISR 2016: 47st International Symposium on Robotics, Munich, Germany, 2016, pp. 1-7.

D. Kaserer, H. Gattringer and A. Müller, "Admittance control of a redundant industrial manipulator without using force/torque sensors," IECON 2016—42nd Annual Conference of the IEEE Industrial Electronics Society, Florence, Italy, 2016, pp. 5310-5315, doi: 10.1109/IECON.2016.7794088.

Villani, L., Sadeghian, H., Siciliano, B. (2013). Null-Space Impedance Control For Physical Human-Robot Interaction. In: Padois, V., Bidaud, P., Khatib, O. (eds) Romansy 19—Robot Design, Dynamics and Control. CISM International Centre for Mechanical Sciences, vol. 544. Springer, Vienna. https://doi.org/10.1007/978-3-7091-1379-0_24.

* cited by examiner

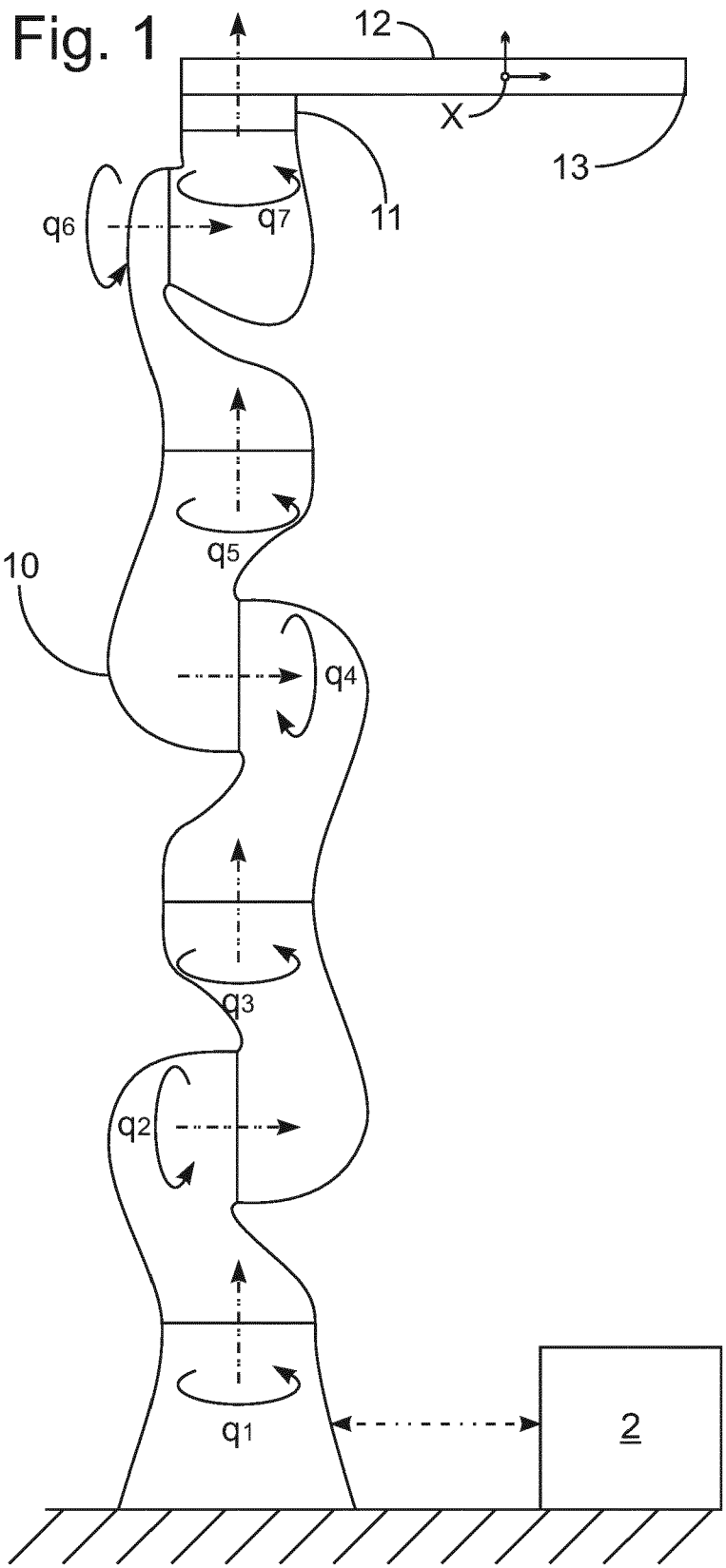

METHOD AND SYSTEM FOR PERFORMING A PREDETERMINED TASK USING A ROBOT

CROSS-REFERENCE TO RELATED APPLICATIONS

This application is a national phase application under 35 U.S.C. § 371 of International Patent Application No. PCT/EP2020/051708, filed Jan. 24, 2020 (pending), which claims the benefit of priority to German Patent Application No. DE 10 2019 202 456.4, filed Feb. 22, 2019, the disclosures of which are incorporated by reference herein in their entirety.

TECHNICAL FIELD

The present invention relates to a method for carrying out a predetermined task using a robot, which is redundant with regard to this task, to a system for operating the robot which is configured to carry out the method, and to a computer program product for carrying out the method.

BACKGROUND

Robots can carry out tasks with regard to which they are redundant. If a task comprises, for example, a predetermined three-dimensional position and three-dimensional orientation of a robot end flange or a robot-guided tool connected thereto, a robot with seven or more consecutive joints is redundant with regard to this task.

On the other hand, hand guiding of robots is known in which the robot follows or evades/tries to evade a force exerted manually thereon.

In previous in-house approaches to hand guiding robots when carrying out a predetermined task, with regard to which the robot is redundant, the precision of carrying out the task in particular is often unsatisfactory.

SUMMARY

The object of the present invention is to improve carrying out predetermined tasks using robots which are redundant with regard to these tasks, preferably to increase the precision of carrying out these tasks with or in spite of hand guiding of the robot.

This object is achieved by a method, and a system or computer program product for carrying out a method as described herein.

According to one embodiment of the present invention, a robot is redundant with regard to a predetermined task. In one embodiment, the robot has more degrees of freedom, in particular joints or axes, than required or determined by the task or for carrying out the task.

If $x_d \in \mathbb{R}^{task}$ or $\dot{x}_d \in \mathbb{R}^{task}$ denote a predetermined task, for example a pose or position and/or orientation of a robot-fixed reference or its change over time, and $q \in \mathbb{R}^{DoF}$ denotes joint coordinates, for example angular positions and orientations, of the robot, then ask <DoF applies accordingly to the ((task-)redundant) robot in an embodiment.

In a further development, the robot has at least six, in particular at least seven, joints or axes, in particular swivel joints or axes (Dof≥6 or Dof≥7), which follow one another in one embodiment, so that said robot can in particular move to any predetermined three-dimensional positions and orientations (Dof≥6) or, with regard to any predetermined six-dimensional poses of robot-fixed references, can always be used redundantly (Dof≥7) and thus very flexibly.

According to one embodiment of the present invention, when carrying out the predetermined task programmed or stored in advance or commanded by an input command in an embodiment, the robot carries out, in particular commands, a motion in a/the zero space (of the robot with regard to the task), which motion is referred to herein as an admittance motion and is dependent on a force exerted externally, in particular manually, on the robot and on a predetermined, in one embodiment configured or parameterized, virtual mass, virtual stiffness and/or virtual damping and is determined on the basis of the force exerted externally on the robot and the predetermined virtual mass, stiffness or damping in one embodiment. In one embodiment, joints or drives of the robot, in one embodiment electric motors, are actuated or commanded in such a way that the robot carries out the task and the admittance motion or is actuated or commanded to carry out the task and the admittance motion.

As a result, in one embodiment, the robot can be hand-guided when carrying out the predetermined task (by externally impressing the force), thereby utilizing its redundancy, in particular for collision avoidance or the like, and thereby advantageously increasing the precision of carrying out the task.

For a more compact representation, an anti-parallel force pair or torque is generally referred to as a force within the meaning of the present invention.

The Jacobian matrix (of the task) is defined in one embodiment in the customary manner by $$J = \frac{\partial x_d}{\partial q} \quad (1)$$

or $$J = \frac{\partial \dot{x}_d}{\partial \dot{q}} \quad (1')$$

with the time derivatives $$\frac{dx_d}{dt} = \dot{x}_d,$$

$$\frac{dq}{dt} = \dot{q},$$

$$\frac{d^2q}{dt^2} = \ddot{q}.$$

A generalized or pseudo inverse $J^\#$ of the Jacobian matrix inversely maps $\dot{x}_d$ to $\dot{q}_d$ $$\dot{q}_d = J^\# \cdot \dot{x}_d \quad (2)$$

and can be defined or determined in an embodiment according to $$J^\# = W^{-1} \cdot J^T \cdot (J \cdot W^{-1} \cdot J^T)^{-1} \quad (3)$$

with the inverse $(\ )^{-1}$ of a weighting matrix W, for example the unit or mass matrix, and the transpose $(\ )^T$.

In one embodiment, the zero space (of the task) is defined in the customary manner by the zero space operator or projector $$N = (1 - J^\# J) \quad (4)$$

In one embodiment, a target admittance motion, in a further development in the joint coordinate space of the robot and/or with the aid of an admittance control, is determined on the basis of the force $T_{ext}$ exerted externally, in particular transformed into the joint coordinate space, on the robot and/or the predetermined virtual mass M, stiffness K and/or damping D, in an embodiment according to $$\ddot{q}_a = M^{-1}(T_{ext} - D \cdot \dot{q}_a - K \cdot q_a) \quad (5)$$

or, in particular by integration or in a control loop, according to $$\dot{q}_a = \dot{q}_a(\ddot{q}_a); \quad (5')$$
$$\text{in particular } \dot{q}_a = \int_t \ddot{q}_a \cdot dt$$

and this determined target admittance motion is projected into the zero space, in one embodiment by left multiplication of the zero space operator N according to Eq. (4).

In one embodiment, K and/or D can be equal to or not equal to zero or the corresponding terms are omitted and/or M can be the identity matrix or different therefrom and from zero.

Such a target admittance motion conveys a motion that a virtual mass, spring and/or damper system, in particular a virtual mass damper system $\ddot{q}_a = M^{-1} \cdot (T_{ext} - D \cdot \dot{q}_a)$ or a virtual mass ($\ddot{q}_a M^{-1} \cdot T_{ext}$) would carry out as a result of the external force $T_{ext}$. As a result, an advantageous behavior of the robot during hand guiding can be implemented in one embodiment.

The force exerted externally on the robot is determined in one embodiment in the joint coordinate space and/or on the basis of forces in the joints of the robot and/or an in particular mathematical or numerical model of the robot; in one embodiment by determining forces in the joints of the robot, in particular by measuring with the aid of sensors, in particular force sensors, or by estimating detected currents in joint drives or the like, in particular with the aid of secondary encoders; and in one embodiment, those internal forces which are determined based on models and/or on the basis of positions and/or motions of the robot, are subtracted from the forces which result from the dynamics, in particular the weight and motions of the robot, in an embodiment according to $$T_{ext} = T_i - (M_m \cdot \ddot{q}_i + h(q_i, \dot{q}_i)) \quad (6)$$

with the determined forces $T_i$ in the joints, the current joint coordinates $q_i$ or their time derivatives, as well as the mass matrix $M_m$ and the vector h of the generalized forces, in particular gyroscopic, gravitational and/or frictional forces, of the robot or its model. As already mentioned, torques are also generally referred to herein as forces. In general, the force exerted externally on the robot is determined in one embodiment on the basis of forces in the joints of the robot that are determined by means of sensors.

As a result, in one embodiment, the force exerted externally on the robot can be determined particularly advantageously, in particular (more) precisely, and hand guiding can thereby be improved.

In one embodiment, the task is or will be specified in the (Cartesian) workspace of the robot.

Additionally or alternatively, in one embodiment the task comprises one or more poses of a robot-fixed reference and/or one or more changes to a pose of a robot-fixed reference, and in one embodiment the task comprises a predetermined motion and/or a predetermined holding of a pose of the robot-fixed reference.

In one embodiment, a pose has a one-, two- or three-dimensional position and/or a one-, two- or three-dimensional orientation, which can in particular be (defined by) such or determine such.

In this way, tasks can advantageously be predetermined or carried out.

In one embodiment, the robot-fixed reference is arranged on a robot-guided tool, in a further development between a tool tip and a robot end flange on which the tool is connected to the robot.

In one embodiment, a robot can be moved in a hand-guided manner while maintaining a fixed point, in particular a trocar point, of a robot-guided, in particular medical, tool with high precision.

In one embodiment, the robot-fixed reference is the "Tool Center Point" (TCP) of the robot.

As a result, it can be positioned with high precision in one embodiment.

Additionally or alternatively, in one embodiment, a target task motion, in particular in the joint coordinate space of the robot, is determined on the basis of the predetermined task, in particular its Jacobian matrix, in particular its generalized or pseudo inverse, in an embodiment according to $$\dot{q}_{task} J^{\#} \cdot \dot{x}_d \quad (7)$$

In one embodiment, the robot is controlled with the aid of a velocity and/or position control on the basis of the target task motion and/or the target admittance motion projected into the zero space, in particular on the basis of a target velocity according to $$\dot{q}_d = \underbrace{J^{\#} \cdot \dot{x}_d}_{\dot{q}_{task}} + N \cdot \dot{q}_a \quad (8)$$

whereby this target velocity can be integrated into a target position in one embodiment. In one embodiment, joints or drives of the robot are thus actuated or commanded on the basis of the target task motion and/or the target admittance motion projected into the zero space.

The present invention can be used with particular advantage in medical robotics. Correspondingly, in one embodiment the robot guides a medical tool, in one embodiment a micro-invasive or non-surgical tool/tool that is not used in surgery. Equally, the present invention can be used with particular advantage in telemanipulation or the robot can be used as a telemanipulator.

According to one embodiment of the present invention, a system for operating the robot, in particular in hardware and/or software, in particular in terms of programming, is configured to carry out a method described here and/or has means for carrying out the task and carrying out an admittance motion that is dependent on a force exerted externally on the robot and on a predetermined virtual mass, stiffness and/or damping in the zero space when the task is carried out.

In one embodiment, the system or its means comprises:
means for determining the force exerted externally on the robot on the basis of forces in joints of the robot and/or a model of the robot; and/or
means for determining a target task motion, in particular in the joint coordinate space of the robot, on the basis of the predetermined task, in particular its Jacobian matrix; and/or
means for determining a target admittance motion, in particular in the joint coordinate space of the robot and/or with the aid of an admittance control, on the basis of the force exerted externally on the robot and/or a predetermined virtual mass, stiffness and/or damping and for projecting this determined target admittance motion into the zero space; and/or a velocity and/or position control on the basis of the task target motion and/or the target admittance motion projected into the zero space.

A means within the meaning of the present invention may be designed in hardware and/or in software, and in particular may comprise a data-connected or signal-connected, in particular, digital, processing unit, in particular microprocessor unit (CPU), graphic card (GPU) having a memory and/or bus system or the like and/or one or multiple programs or program modules. The processing unit may be designed to process commands that are implemented as a program stored in a memory system, to detect input signals from a data bus and/or to output signals to a data bus. A storage system may comprise one or a plurality of, in particular different, storage media, in particular optical, magnetic, solid-state and/or other non-volatile media. The program may be designed in such a way that it embodies or is capable of carrying out the methods described herein, so that the processing unit is able to carry out the steps of such methods and thus, in particular, is able to control or regulate the robot. For the sake of a more compact representation, in the present case regulation is also generally referred to as controlling. In one embodiment, a computer program product may comprise, in particular, a non-volatile storage medium for storing a program or comprise a program stored thereon, an execution of this program prompting a system or a controller, in particular a computer, to carry out the method described herein or one or multiple of steps thereof.

In one embodiment, one or multiple, in particular all, steps of the method are carried out completely or partially automatically, in particular by the system or its means.

In one embodiment, the system comprises the robot and/or its controller.

In one embodiment, time derivatives can be implemented by corresponding differences, for example the task $\dot{x}_d$ by a differential command $\Delta x_d$, the target velocity $\dot{q}_d$ by a differential command $\Delta q_d$, etc.

Further advantages and features will be apparent from the accompanying drawings and the description thereof.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

FIG. 1 illustrates a system for operating a robot or for carrying out a predetermined task using the robot according to an embodiment of the present invention; and FIG. 2 illustrates a method for carrying out the task using the robot according to an embodiment of the present invention.

DETAILED DESCRIPTION

FIG. 1 shows a system with a controller 2 for controlling or regulating a seven-axis robot 10 or for carrying out a predetermined task using the robot 10 according to an embodiment of the present invention, and FIG. 2 shows a method for carrying out the task using the robot according to an embodiment of the present invention.

The robot 10 guides a tool 12 which is fastened to the robot end flange 11 and comprises a distal tool tip 13.

A predetermined task is, for example, to keep the three-dimensional Cartesian position of the tool-fixed point X constant. Another predefined task can be, for example, a predefined TCP pose or TCP path.

In a first step S10, the controller 2 determines forces, in particular torques Ti about the (rotational) axes, in the joints of the robot, for example by means of force, in particular torque sensors in the joints (not shown).

In a second step S20, the controller 2 uses this to determine a force Text exerted externally on the robot, for example according to Eq. (6) or in another way.

In a third step S30, the controller 2 determines a target admittance motion $\dot{q}_a$ or $\ddot{q}_a$ on the basis of this force Text exerted externally on the robot and a predetermined virtual mass M and damping D, with the aid of an admittance control, for example according to Eq. (5), (5') with K=0 or in another way.

In a fourth step S40, the controller 2 projects this target admittance motion into the zero space of the task, adds a task target motion that it determines on the basis of the generalized or pseudo inverse of the Jacobian matrix of the predetermined task, for example according to Eq. (7) or in another way, and feeds the resulting or according to Eq. (8) determined target motion ad, possibly after integration into a target position $q_d$ in the joint coordinate space, to a velocity or position control, which commands the corresponding joint angle or controls drives of the robot 10 (not shown) accordingly.

As a result, when carrying out the task in the zero space, the robot 10 carries out an admittance motion $\dot{q}_a$ that is dependent on the force exerted externally on the robot and on the predetermined virtual mass and damping.

Although embodiments have been explained in the preceding description, it is noted that a large number of modifications are possible. It is also noted that the embodiments are merely examples that are not intended to restrict the scope of protection, the applications and the structure in any way. Rather, the preceding description provides a person skilled in the art with guidelines for implementing at least one embodiment, with various changes, in particular with regard to the function and arrangement of the described components, being able to be made without departing from the scope of protection as it arises from the claims and from these equivalent combinations of features.

While the present invention has been illustrated by a description of various embodiments, and while these embodiments have been described in considerable detail, it is not intended to restrict or in any way limit the scope of the appended claims to such de-tail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

REFERENCE NUMERALS

10 Robot
11 Robot end flange
12 Robot-guided tool

13 Tool tip
2 Controller
$q_1, \ldots q_7 = q$ Joint coordinates/angles
X Robot-fixed reference

What is claimed is:

1. A method for carrying out a predetermined task using a robot, wherein the robot is redundant with regard to the task, the method comprising:
   executing the task by actuating at least one joint of the robot, while performing an admittance motion in the null space of the robot in response to the command;
   wherein the admittance motion is based on a force exerted externally on the robot and at least one of a predetermined virtual mass, a predetermined virtual stiffness, or a predetermined virtual damping associated with the robot;
   wherein a determined target admittance motion is projected into the null space; and
   the target admittance motion is determined on the basis of at least one of:
      the force exerted externally on the robot, or
      at least one of a predetermined virtual mass, stiffness, or damping.

2. The method of claim 1, further comprising:
   determining the force exerted externally on the robot based on at least one of forces in the joints of the robot or a model of the robot.

3. The method of claim 1, wherein at least one of:
   the task is predetermined in the workspace of the robot; or
   the task comprises at least one of:
      at least one pose of the robot, or
      at least one change of pose of a robot-fixed reference.

4. The method according of claim 3, wherein at least one of:
   the robot-fixed reference is arranged on a robot-guided tool; or
   at least one of the tool center point (TCP) of the robot or a target task motion is determined on the basis of the predetermined task.

5. The method of claim 4, wherein at least one of:
   the robot-fixed reference is arranged on the robot-guided tool between a tool tip and a robot end flange;
   the target task motion is in the joint coordinate space of the robot; or
   the TCP of the robot or the target task motion is determined on the basis of the Jacobian matrix of the predetermined task.

6. The method of claim 4, further comprising:
   controlling motion of at least one joint of the robot using at least one of velocity control or position control;
   wherein the velocity control or the position control is based on at least one of:
      the target task motion, or
      the target admittance motion projected into the null space.

7. The method of claim 1, wherein the target admittance motion is at least one of:
   in the joint coordinate space of the robot; or
   performed with the aid of an admittance control.

8. The method of claim 1, further comprising:
   controlling motion of at least one joint of the robot using at least one of velocity control or position control;
   wherein the velocity control or the position control is based on the target admittance motion projected into the null space.

9. The method of claim 1, wherein executing the predetermined task comprises guiding a medical tool with the robot.

10. The method of claim 1, wherein the target admittance motion is determined on the basis of:
    the force exerted externally on the robot; and
    at least one of a predetermined virtual mass, stiffness, or damping.

11. A system for operating a robot to carry out a predetermined task, wherein the robot is redundant with regard to the task, the system comprising:
    a robot controller configured to execute the task while performing an admittance motion in the null space of the robot;
    wherein the admittance motion is based on a force exerted externally on the robot and at least one of a predetermined virtual mass, a predetermined virtual stiffness, or a predetermined virtual damping associated with the robot;
    wherein a determined target admittance motion is projected into the null space; and
    wherein the target admittance motion is determined on the basis of at least one of:
       the force exerted externally on the robot, or
       at least one of a predetermined virtual mass, stiffness, or damping.

12. A computer program product for carrying out a predetermined task using a robot, wherein the robot is redundant with regard to the task, the computer program product comprising program code stored on a non-transient computer-readable medium, the program code, when executed on a computer, causing the computer to:
    execute the predetermined task by actuating at least one joint of the robot; and
    perform an admittance motion in the null space of the robot while executing the predetermined task;
    wherein the admittance motion is based on a force exerted externally on the robot and at least one of a predetermined virtual mass, a predetermined virtual stiffness, or a predetermined virtual damping associated with the robot;
    wherein a determined target admittance motion is projected into the null space; and
    wherein the target admittance motion is determined on the basis of at least one of:
       the force exerted externally on the robot, or
       at least one of a predetermined virtual mass, stiffness, or damping.

* * * * *